US008495765B2

(12) United States Patent
Araki et al.

(10) Patent No.: US 8,495,765 B2
(45) Date of Patent: Jul. 30, 2013

(54) SOCK (75) Inventors: Takahiro Araki, Nara (JP); Yuko Yanagisawa, Nara (JP); Masaaki Makikawa, Kusatsu (JP)

(73) Assignees: Okamoto Corporation, Nara (JP); Ritsumeikan University, Shiga (JP)

( * ) Notice: Subject to any disclaimer, the term of this patent is extended or adjusted under 35 U.S.C. 154(b) by 419 days.

(21) Appl. No.: 12/342,841

(22) Filed: Dec. 23, 2008

(65) Prior Publication Data
US 2009/0165190 A1 Jul. 2, 2009

(30) Foreign Application Priority Data

Dec. 27, 2007 (JP) ................................. 2007-336224

(51) Int. Cl.
*A43B 17/00* (2006.01)
(52) U.S. Cl.
USPC ............................................. 2/240; 66/178 A
(58) Field of Classification Search
USPC ................ 2/240, 239, 241, 242, 409; 66/182, 66/183, 184, 185, 186, 187, 178 A; 602/63, 602/65, 66
See application file for complete search history.

(56) References Cited

U.S. PATENT DOCUMENTS

| 2,050,535 | A | * | 8/1936 | Martel | 66/178 R |
| 2,102,368 | A | * | 12/1937 | Martel | 66/182 |
| 2,120,665 | A | * | 6/1938 | Crimmins | 66/190 |
| 2,219,235 | A | * | 10/1940 | Morton | 2/239 |
| 3,290,904 | A | * | 12/1966 | Snyder | 66/200 |
| 4,253,317 | A | * | 3/1981 | Howard et al. | 66/186 |
| 4,522,044 | A | * | 6/1985 | Lineberry et al. | 66/185 |
| 5,335,517 | A | * | 8/1994 | Throneburg et al. | 66/185 |
| 5,412,957 | A | * | 5/1995 | Bradberry et al. | 66/178 A |
| 5,473,781 | A | * | 12/1995 | Greenberg | 2/239 |
| 5,617,745 | A | * | 4/1997 | Della Corte et al. | 66/178 A |
| 5,771,495 | A | * | 6/1998 | Turner et al. | 2/239 |
| 6,012,177 | A | * | 1/2000 | Cortinovis | 2/239 |
| 6,805,681 | B2 | * | 10/2004 | Yokoyama | 602/65 |
| 7,192,411 | B2 | * | 3/2007 | Gobet et al. | 602/63 |
| 2006/0085894 | A1 | * | 4/2006 | Yakopson et al. | 2/239 |
| 2007/0113593 | A1 | * | 5/2007 | Jeong | 66/180 |
| 2007/0283483 | A1 | * | 12/2007 | Jacober | 2/239 |

FOREIGN PATENT DOCUMENTS

| JP | 2005-312512 A | 11/2005 |
| JP | 2006-225833 A | 8/2006 |

* cited by examiner

*Primary Examiner* — Khoa Huynh
*Assistant Examiner* — Anna Kinsaul
(74) *Attorney, Agent, or Firm* — Brinks Hofer Gilson & Lione (57) ABSTRACT

A sock is provided having a first compression area 1 which raises the compressive force in a wale direction from a position A behind the toe area of a sole portion of the sock to a position C which includes the boundary between an arch portion B and a heel portion 6, a second compression area 2 provided on the periphery to raise the compressive force in a course direction at the position A behind the toe area, a third compression area 3 provided on the periphery to raise the compressive force in a course direction at an ankle portion D, and a fourth compression area 4 provided on the periphery to raise the compressive force in a course direction from the position C which includes the boundary between the arch portion B and the heel portion 6 to a position E at the base of the instep portion. The advantageous effect of protecting and restoring the shape of the longitudinal plantar arch is produced by the various compression areas, thereby stabilizing the position of the various compression areas while the sock is worn.

12 Claims, 9 Drawing Sheets

Oblique shape (b)

Rounded shape

N21 : First metatarsal
N22 : Fifth metatarsal
N31 : Calcaneal tubercle
N32 : Left side of arch
N33 : Right side of arch

(b)

P1 Longitudinal plantar arch

P2 Transverse plantar arch

Figure 11

SOCK

RELATED APPLICATIONS

The present application claims priority to Japanese Patent Application Number 2007-336224, filed Dec. 27, 2007, the entirety of which is hereby incorporated by reference.

TECHNICAL FIELD

The present invention relates to a sock which maintains a normal shape of a longitudinal plantar arch and a transverse plantar arch formed by bones of the foot, ligaments, and a group of plantar muscles, by securely positioning a compression area which raises the compressive force in a desired direction at a suitable position on the foot, thereby making it possible to prevent a variety of foot injuries.

BACKGROUND ART

Figure 9:
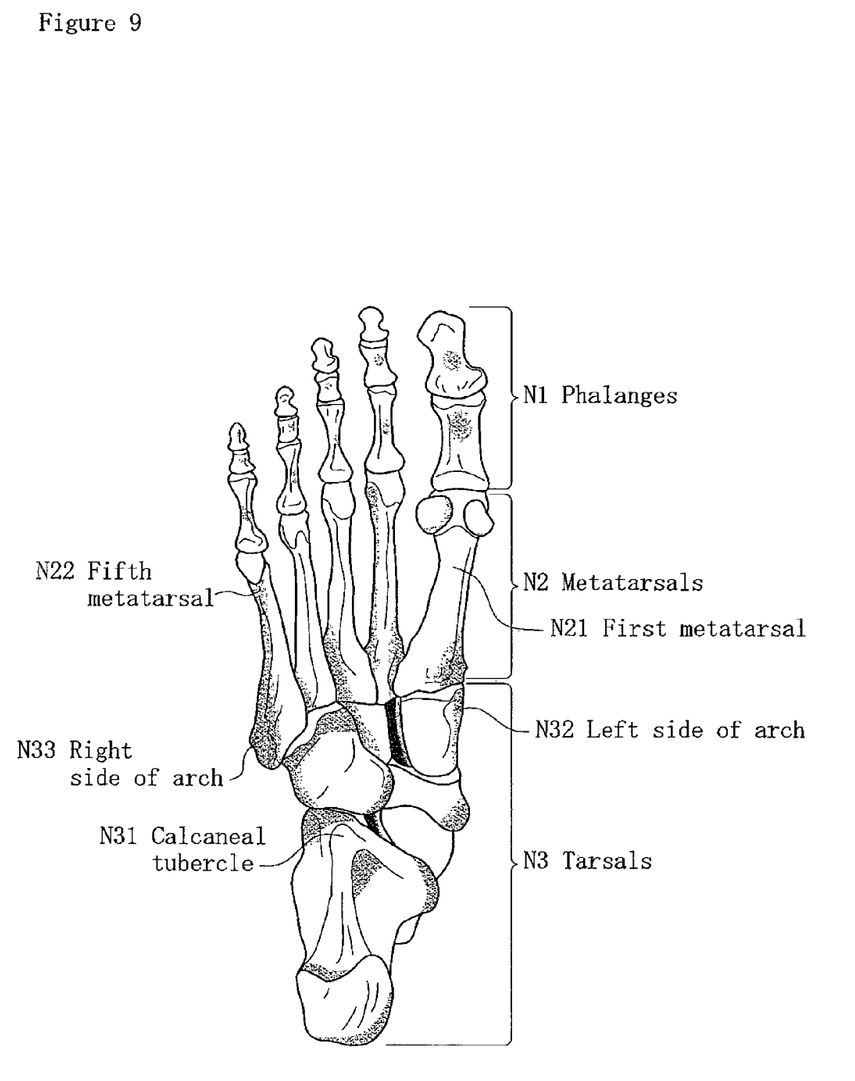
FIG. 9 is a drawing illustrating the configuration of the bones of a right human foot as seen from the bottom side of the foot.
Figure 11:
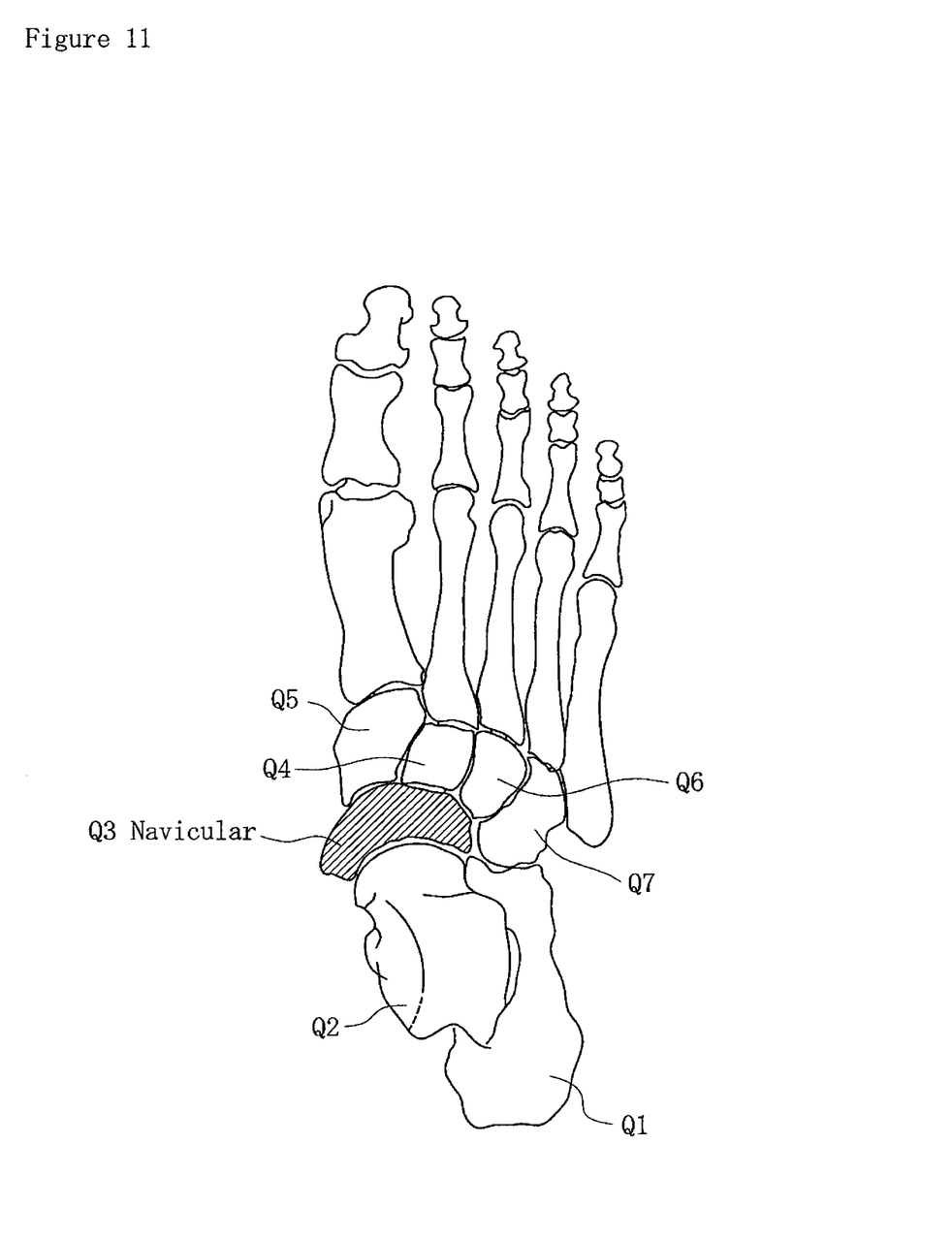
FIG. 11 shows the configuration of the bones of a right human foot as seen from the instep side, and illustrates the 7 bones that form the tarsals.

FIG. 9 shows the configuration of the bones of a right human foot as seen from the bottom side of the foot. FIG. 11 shows the configuration of the bones of a right human foot as seen from the instep side. As shown in FIG. 9 and FIG. 11, the bones of the human foot consist of the tarsals N3, which include the calcaneus Q1, the talus Q2, the navicular Q3, the cuneiform bones Q4-Q6, and the cuboid Q7, as well as the 5 metatarsals N2, and the phalanges N1.

Figure 10:
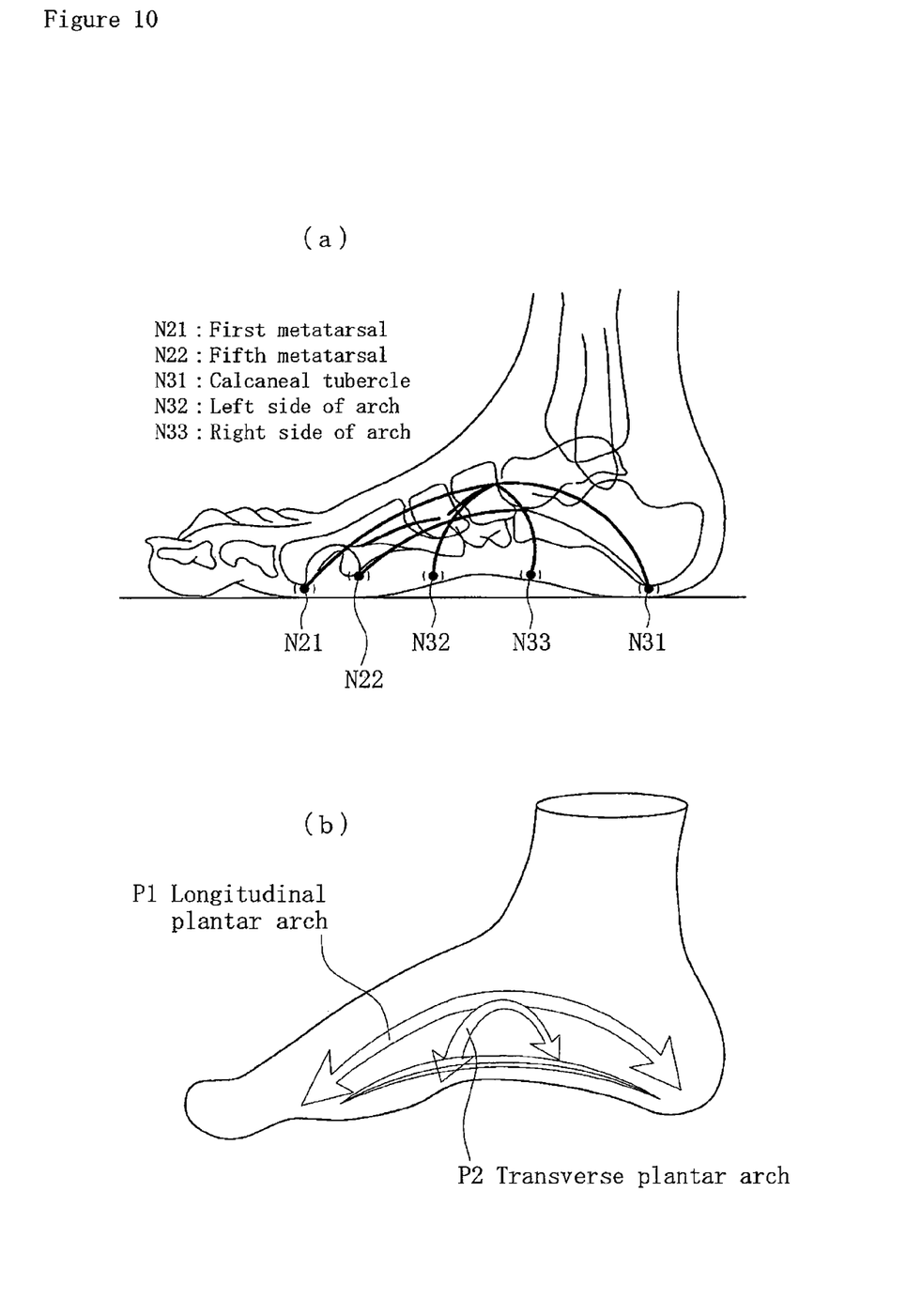
FIG. 10(a) is a drawing illustrating the inside arch and the outside arch forming an arch formed across the first or the fifth metatarsal with the calcaneal tubercle as the starting point, and the anterior arch which is formed from the first metatarsal to the fifth metatarsal, and a primary arch which is formed from the left side to the right side of the arch of the foot.
FIG. 10(b) is a drawing illustrating the longitudinal plantar arch and the transverse plantar arch.

The joints of the bones that form the foot are strongly bound to each other by ligaments, and form the skeletal structure of the foot. Since a group of plantar muscles formed from soft tissues such as the metatarsal muscles, thenar muscles, and antithenar muscles is present on the bottom of the foot, the shape of the bottom of the foot further increases the stability. As shown in FIG. 10(b), longitudinal plantar arch P1 (arch in the longitudinal direction) and transverse plantar arch P2 (arch in the longitudinal direction) are formed on the bottom of the foot from these bones, ligaments, and group of plantar muscles.

As shown in FIGS. 9 and 10(a), the longitudinal plantar arch P1 is formed from an inside arch (inside longitudinal arch) which extends across the talus, the navicular, and the inside cuneiform bones to the first metatarsal N21, and from an outside arch (outside longitudinal arch) forming an arch which extends across the cuboid to the fifth metatarsal N22, the arch having a starting point of the calcaneal tubercle N31. On the other hand, as shown in FIG. 9 and FIG. 10(a), the transverse plantar arch P2 is formed from an anterior arch which extends from the first metatarsal N21 to the fifth metatarsal N22, and a primary arch which extends from the left side N32 to the right side N33 of the arch of the foot, including the 3 cuneiform bones.

Accordingly, the longitudinal planar arch P1 (inner longitudinal arch, outer longitudinal arch) formed from bones, ligaments, and a group of plantar muscles, and the transverse plantar arch P2 (anterior arch, primary arch) are formed on the bottom of the foot. The arch structures of the sole of the foot formed from these four arches do not represent independent entities, but rather, are mutually related in forming the arch of the foot, and serve as: 1) a spring to soften the impact of the foot touching the ground while walking; 2) to distribute the body weight over the entire foot; and 3) to play an important role in making for a smooth shifting of body weight. It is therefore thought that maintaining a normal shape for the longitudinal plantar arch P1 and the transverse plantar arch P2 is also related to preventing a variety of foot injuries.

However, when the plantar ligaments and the group of plantar muscles stretch excessively due to vigorous exercise and walking for long periods of time, it becomes impossible to maintain the arch shapes of the longitudinal plantar arch P1 and the transverse plantar arch P2 and a shock-absorbing effect is not sufficiently achieved during walking, thus it becomes impossible to achieve a sufficient spring-like function, consequently causing the feet to tire and the body to feel languid. Furthermore, since the bottoms of the feet are unable to absorb shock, this can affect the joints of the feet, the knees, and the groin. In severe cases, this excessive stretching may affect the hips and the shoulders, making it necessary to undergo treatment at a hospital.

Accordingly, there have been disclosed socks which aimed to restore an almost normal state to the transverse arch and to the longitudinal arch of the sole of the foot which had lost their shape or had been lost altogether due to shoes that did not fit.

For example, Japanese Laid-Open Patent Application No. 2005-3125121, a sock is disclosed having a structure in which there is provided an elastic expanding member in the width direction of the foot having a tension resistance force greater than other parts in at least a part corresponding to the side of the bottom of the foot of the transverse ligament, among the parts corresponding to the bottom side of the foot from the first to fifth materials, and a part corresponding to the dorsal side of the tarsals.

However, the sock of Japanese Laid-Open Patent Application No. 2005-3125121 gives priority to preventing the development of conditions such as poor blood circulation and chilblain, and does not provide an elastic expanding member for the entire periphery in the course direction of the sock. Therefore, since the position of the elastic expanding member slips while the sock is being worn, there is the problem in that the sock does not impart a continuous compressive force at the desired position, making it impossible to achieve much of an advantageous effect, even if an elastic expanding member is provided with the aim of restoring the transverse arch and the longitudinal arch.

In Japanese Laid-Open Patent Application No. 2006-225833 is disclosed a sock having a structure with a network of highly elastic areas which connect at least an area which traverses the arch portion and an area which traverses the upper portion of the calcaneus.

However, since the sock of Japanese Laid-Open Patent Application No. 2006-225833 imparts an upward force on the upper portion of the calcaneus from the position of the arch due to the highly elastic areas in an upper diagonal direction, but no consideration was given to protecting and restoring the transverse plantar arch and the sock fails to protect the longitudinal plantar arch by lifting the arch straight upward and to restore the longitudinal plantar arch to its original shape.

In addition, in the sock of Japanese Laid-Open Patent Application No. 2006-225833, since the highly elastic areas which are divided right and left by the arch portion are continued again from the back of the heel, when the sock is worn, it is possible to prevent it from slipping forward from the arch position, but a problem exists in that it is impossible to prevent the position of the highly elastic areas to slip backward from the arch position. Accordingly, since the position of the highly elastic areas slips while wearing the sock, it is impossible to continuously raise the arch.

The present invention was devised with the problems of conventional socks in mind, and has as one of its objects to provide a sock which is able to maintain a normal shape of both the longitudinal plantar arch and the transverse plantar arch formed by the bones of the foot, the ligaments, and a group of plantar muscles, by securely positioning compression areas at a suitable position on the foot, without the compression areas slipping when the sock is worn.

SUMMARY OF THE INVENTION

Socks are described below that may allow for maintaining a normal shape of both the longitudinal plantar arch and the transverse plantar arch formed by the bones of the foot, the ligaments, and a group of plantar muscles. This may be accomplished by securely positioning compression areas at a suitable position on the foot, without the compression areas slipping when the sock is worn. The invention may include any of the following aspects in various combinations and may also include any other aspect described below in the written description or in the attached drawings. In one aspect, the sock comprises a first compression area which raises the compressive force in a wale direction from a position behind a toe area of a sole portion of the sock to a position which includes the boundary between an arch portion and a heel portion. The sock further includes a second compression area provided on a periphery of the sock to raise the compressive force in a course direction at a position behind the toe area, and a third compression area provided on the periphery to raise the compressive force in a course direction at an ankle portion. A fourth compression area is provided on the periphery of the sock to raise the compressive force in a course direction from a position which includes the boundary between an arch portion and a heel portion to a position at the base of the instep portion.

In another aspect, the first compression area and the second compression area are continuous at the position behind the toe area of the sole portion, and the first compression area and the fourth compression area are continuous at a position which includes the boundary between the arch portion and the heel portion. The fourth compression area and the third compression areas may be continuous from the position of the base of the instep portion to the ankle portion, without separating.

In yet another aspect, the first through the fourth compression areas may have increased compressive force in a desired direction, due to the use of either one or both of a knitted structure with increased expandability, or a material with high expandability. The first through the fourth compression areas may be knit using tuck knitting for a knit structure with increased expandability, and using rubber yarns and FTY as materials with high expandability. In one embodiment, the rubber yarns may be elastic yarns having core yarns with a thickness of between about 120 D and 680 D.

In another embodiment, the first through the fourth compression areas may have a tensile force in the wale direction of the fabric within a range of about 3.5 to about 6.0 N, and a tensile force of the fabric in the course direction of the fabric within a range of about 5.0 to about 9.0 N. The tensile force of the fabric of the first through the fourth compression areas may be the same tensile force.

In another aspect, the gore line on the little toe side may be made longer than on the big toe side, the front end of the toe portion may be shifted from the position of tip of the third toe to the side of the big toe, and the end of the gore line on big toe side is positioned on the inner side of the big toe. The shape of the toe portion, when viewed from a planar perspective, may be formed in an oblique shape.

In still another aspect, a gore line may run diagonally from a starting point in the vicinity of the anklebone to the end of the heel portion, and the heel portion may be made to cover the entire heel by having the starting point of the gore line approach the position of the base of the instep portion.

In one embodiment, the inside surface of the toe portion and the heel portion are both knit with pile knitting, and the pile length of the heel portion is made longer than the pile length of the toe portion.

In one aspect, components other than the first through the fourth compression areas are knit with two or more highly water-absorbent and quick-drying materials. The highly water-absorbent and quick-drying materials may be selected from a group consisting of polyester, acrylic, wool, rayon, or cotton.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 6 is an explanatory diagram of the shape of the human foot, where FIG. 6(a) shows feet with an oblique shape, and FIG. 6(b) shows feet with a rounded shape.

PREFERRED EMBODIMENTS

The problems to be solved are that in the conventional socks, (1) no consideration was given to protecting or restoring either the longitudinal plantar arch or the transverse plantar arch; and (2) since the position of the compression areas slipped while wearing the sock, it was impossible to continuously impart a compressive force at the desired position.

In order to solve the above problems, the sock of the present invention is provided with a first compression area which raises the compressive force in a wale direction from a position behind a toe area of a sole portion of the sock to a position which includes the boundary between an arch portion and a heel portion, and a second compression area provided on the periphery to raise the compressive force in a course direction at a position behind the toe area, and a third compression area provided on the periphery to raise the compressive force in a course direction at an ankle portion, and a fourth compression area provided on the periphery to raise the compressive force in a course direction from a position which includes the boundary between an arch portion and a heel portion to a position at the base of the instep portion.

According to the present invention, since a second compression area is provided at an anterior arch position of the transverse plantar arch, and since a fourth compression area is provided at a primary arch of the transverse plantar arch, a compressive effect is obtained in the course direction at the respective positions, thereby producing the advantageous effects of protecting and restoring the shape of the transverse plantar arch. Furthermore, since the first compression area, which is securely positioned by the second compression area and the fourth compression area, pushes up the longitudinal plantar arch from below, there is obtained the advantageous effect of protecting and restoring the shape of the longitudinal plantar arch, so that the entire sock is restrained from slipping forward and backward by the third compression area provided at the ankle portion, thereby stabilizing the position of the various compression areas while the sock is worn.

The sock of the present invention has a structure including a first compression area which raises the compressive force in a wale direction from a position behind a toe area of a sole portion of the sock, and a second compression area provided on the periphery to raise the compressive force in a course direction at a position behind a toe area, and a third compression area provided on the periphery to raise the compressive force in a course direction at an ankle portion, and a fourth compression area provided on the periphery to raise the compressive force in a course direction from a position which includes the boundary between an arch portion and a heel portion to a position at the base of the instep portion (the first embodiment of the present invention).

In a sock of the first embodiment of the present invention, in particular, when the embodiment is such that when the first compression area and the second compression area are caused to be continuous at the position behind the toe area of the sole portion, and the first compression area and the fourth compression area are caused to be continuous at a position which includes the boundary between the arch portion and the heel portion, and the fourth compression area and the third compression area are caused to be continuous from the position of the base of the instep portion to the ankle portion without separating (the second embodiment of the present invention), since the first through the fourth compression areas are mutually positioned to be able to reliably prevent slipping of the sock, the advantageous effects of the present invention are more suitably put into effect.

In the present invention, there are no particular limitations on the means for providing increased compressive force to the first through the fourth compression areas. Methods can be used such as producing a knit structure with increased expandability, or a method of using a highly expandable material, or a method of adhering or attaching an elastic member. However, in a sock of the first or second embodiments, in particular, in cases where the first through the fourth compression areas have increased compressive force in a desired direction, due to the use of either one or both of a knitted structure with increased expandability, or a material with high expandability (the third embodiment of the present invention), it is possible to produce a sock of the present invention by an ordinary sock knitting process using a sock knitting machine, without separately employing a special process such as adhering or attaching an elastic member, and is therefore suitable.

In a sock of the third embodiment, in particular, in cases where the first through the fourth compression areas are knit using tuck knitting for a knit structure with increased expandability, and using rubber yarns and FTY as materials with high expandability (the fourth embodiment of the present invention), the response range broadens due to a synergetic effect of compressive force of the knit structure due to tuck knitting and the compressive force of the material due to the rubber yarns, thereby making it possible to impart sufficient compressive force to the various compression areas, even though the shape of the foot of the sock wearer varies from person to person.

In a sock of the fourth embodiment, in particular, when the embodiment is such that the rubber yarns are elastic yarns having core yarns with a thickness of 120 D-680 D (the fifth embodiment of the present invention), the compressive force of the various compressive areas does not readily decrease, even with repeated wearing, washing, and drying, and is therefore suitable.

In the present invention, there are no particular limitations on the tensile force of the fabric of the first through the fourth compression areas, and it can be set in a suitable range which takes into consideration the feeling of comfort while wearing the sock. However, if the compressive force is increased excessively, there is a risk of impairing blood circulation in the foot. Conversely, if the compressive force is insufficient, the resulting slip-preventing effect while wearing the sock is insufficient, and the resulting effect of protecting the arch of the bottom of the foot may be insufficient.

Accordingly, research conducted by the present inventors showed that in the sock of any one of the first to the fifth embodiments, in particular in the case of the first through the fourth compression areas, if the tensile force of the fabric in the wale direction is set in a range of 3.5-6.0 N, and the tensile force of the fabric in the course direction is set in a range of 5.0-9.0 N (the sixth embodiment of the present invention), in addition to the fact that there is no risk of impairing blood circulation in the foot or chilblain, sufficient compressive force is produced to prevent slipping while the sock is worn, and to protect and restore the shape of the longitudinal plantar arch and the transverse plantar arch on the bottom of the foot.

According to research conducted by the present inventors, if the tensile force of the fabric is within the above ranges, there is no need to make fine adjustments to the tensile force of the fabric of each of the first through the fourth compression areas. Accordingly, in a sock of the sixth embodiment, if the tensile force of the fabric of the first through the fourth compression areas is the same tensile force, the design of the sock does not become complex, and this is advantageous (the seventh embodiment of the present invention).

In the sock of the present invention, there may not be any particular limitations on the structure of components other than the first through the fourth compression areas, such as the toe portion or the heel portion, and a variety of embodiments may be employed, depending on the manufacturer's concept of the product, and depending on the preferences of the consumer.

However, in a sock of any of the first through the seventh embodiments of the present invention, in particular, in the toe portion, if the gore line on the little toe side is made longer than on the big toe side, and the front end of the toe portion is shifted from the position of tip of the third toe to the side of the big toe, and the end of the gore line on the big toe side is positioned on the inner side of the big toe (the eighth embodiment of the present invention), then the shape of the toe portion of the sock may be made to approximate an oblique shape of a foot having a characteristic curve in which there is a peak at the big toe, and a gradual shortening as it approaches the little toe, thereby eliminating the tugging feeling on the inner side of the big toe which is felt when a conventional sock is worn. This increases the feeling of comfort, and is therefore suitable.

Figure 6:
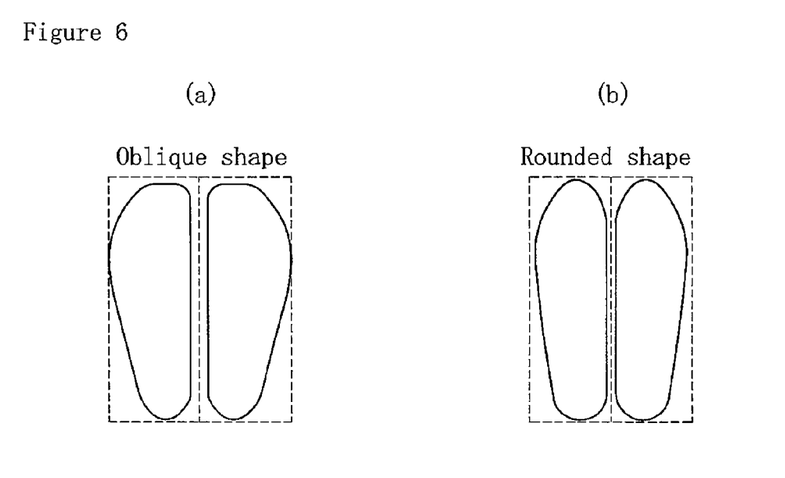

Generally, the shape of the human foot can be described as being either oblique or rounded. FIG. 6 is an explanatory diagram, where FIG. 6(*a*) shows feet with an oblique shape, and FIG. 6(*b*) shows feet with a rounded shape.

As shown in FIG. 6(*a*), the oblique shape is a shape of a foot having a characteristic curve in which there is a peak at the big toe, and a gradual shortening as it approaches the little toe. In the oblique shape, the line from the inner side of the big toe to the heel is almost a straight line.

By contrast, as shown in FIG. 6(*b*), the rounded shape is a shape of a foot having a curve which is right-left symmetrical, with a peak at the second or third toe.

In conventional socks, an approximately rounded toe portion is employed so as to simplify the process for producing the toe portion. However, it has been reported that the oblique shape makes up 60-80% of foot shapes of Japanese people. If people with an oblique foot shape wear a sock with a toe portion with an approximately rounded shape, the inside part of the big toe is subjected to a reactive force from the inner surface of the toe portion of the sock, so there is a constant tugging feeling, resulting in discomfort while wearing the sock.

Accordingly, if a sock is structured according to the eighth embodiment of the present invention, a toe portion is produced which has approximately an oblique shape, thereby increasing the comfort while wearing the sock. Furthermore, if the shape of the toe portion, when viewed from a planar perspective, is formed in an oblique shape by adjusting the number of angles of the toe portion (the ninth embodiment of the present invention), this makes it possible to reduce the reactive force to which the inside part of the big toe is subjected from the inner surface of the toe portion of the sock (feeling of tugging of the toe portion) to an almost imperceptible level, so as to produce a comfortable feeling.

A sock of any one of the first to the ninth embodiments can be provided with a gore line which runs diagonally from a starting point in the vicinity of the anklebone to the end of the heel portion, and in this case, in particular, if the heel portion is made to cover the entire heel, by having the starting point of the gore line approach the position of the base of the instep portion (the tenth embodiment of the present invention), then the heel portion completely encloses the entire heel, making it possible to obtain an effect such that slipping does not readily occur while the sock is worn, and is therefore suitable.

In a sock of any one of the first to the tenth embodiments, in particular, if the inside surface of the toe portion and the heel portion are both knit with pile knitting, and the pile length of the heel portion is made longer than the pile length of the toe portion (the eleventh embodiment of the present invention), then priority is given to the shock-absorbing capacity with a pile knit having longer piles for the heel portion, which receives the most impact when making contact with the ground during walking. Furthermore, the use of pile knitting with piles of short length in the toe portion, upon which is exerted a force when the foot hits the ground to generate thrust for walking, ensures that this force will be exerted, thereby making it possible to soften the impact on the toe portion when this force is exerted, and is therefore suitable.

In a sock of any one of the first to the eleventh embodiments, in particular, if components other than the first through the fourth compression areas are knit with two or more highly water-absorbent and quick-drying materials including polyester, acrylic, wool, rayon, or cotton (the twelfth embodiment of the present invention), then it is possible to expedite sweat absorption and drying, and to reduce the moist feeling during walking or running, and is therefore suitable.

Specifically, greater air permeability can be obtained, and a more comfortable sock can be provided by using yarns with an acrylic/cotton mixture having outstanding water absorption and quick-drying properties.

Example

Figure 1:
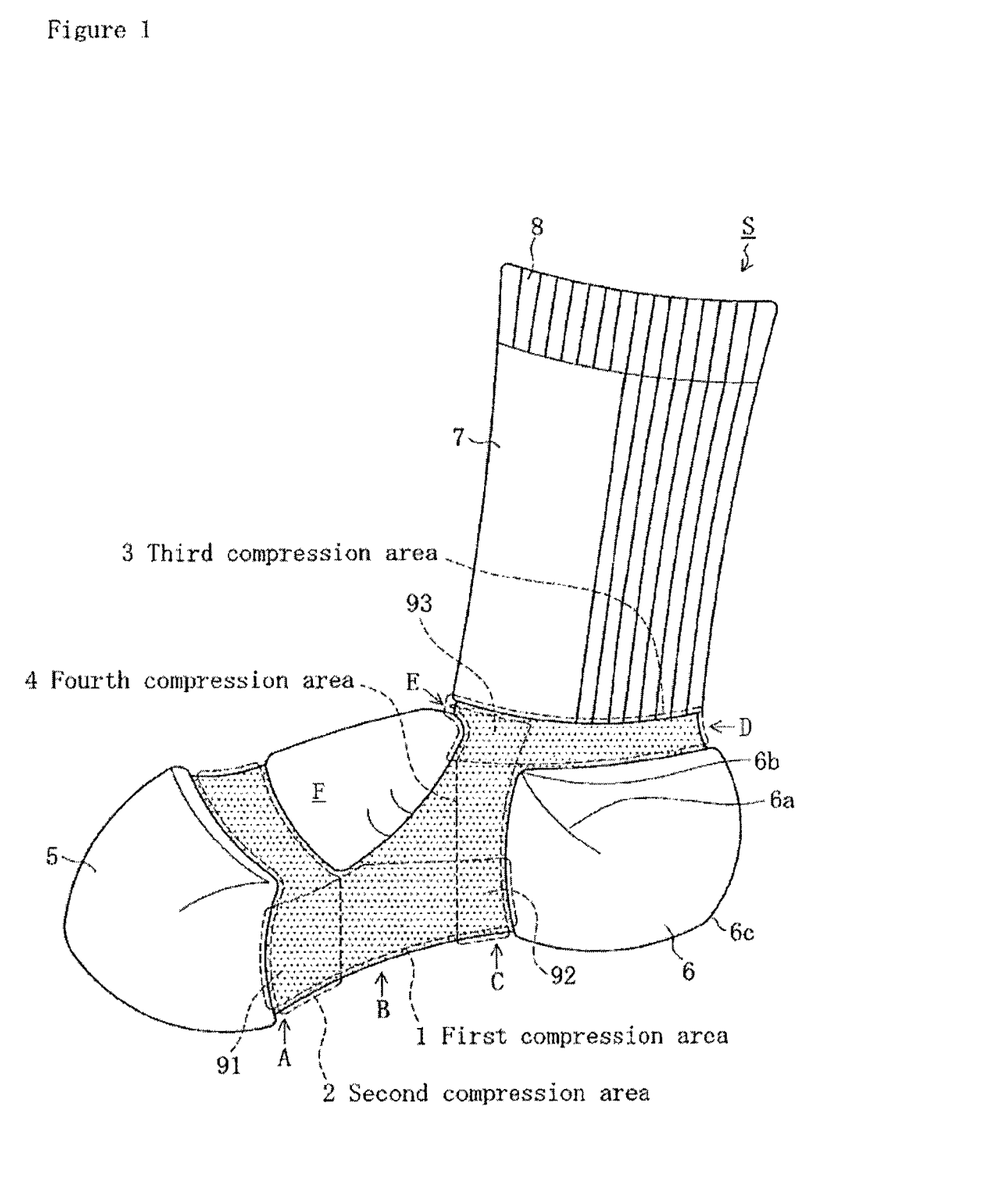
FIG. 1 is a lateral view of a sock of the present invention for the right foot as seen from the side of the big toe.
Figure 2:
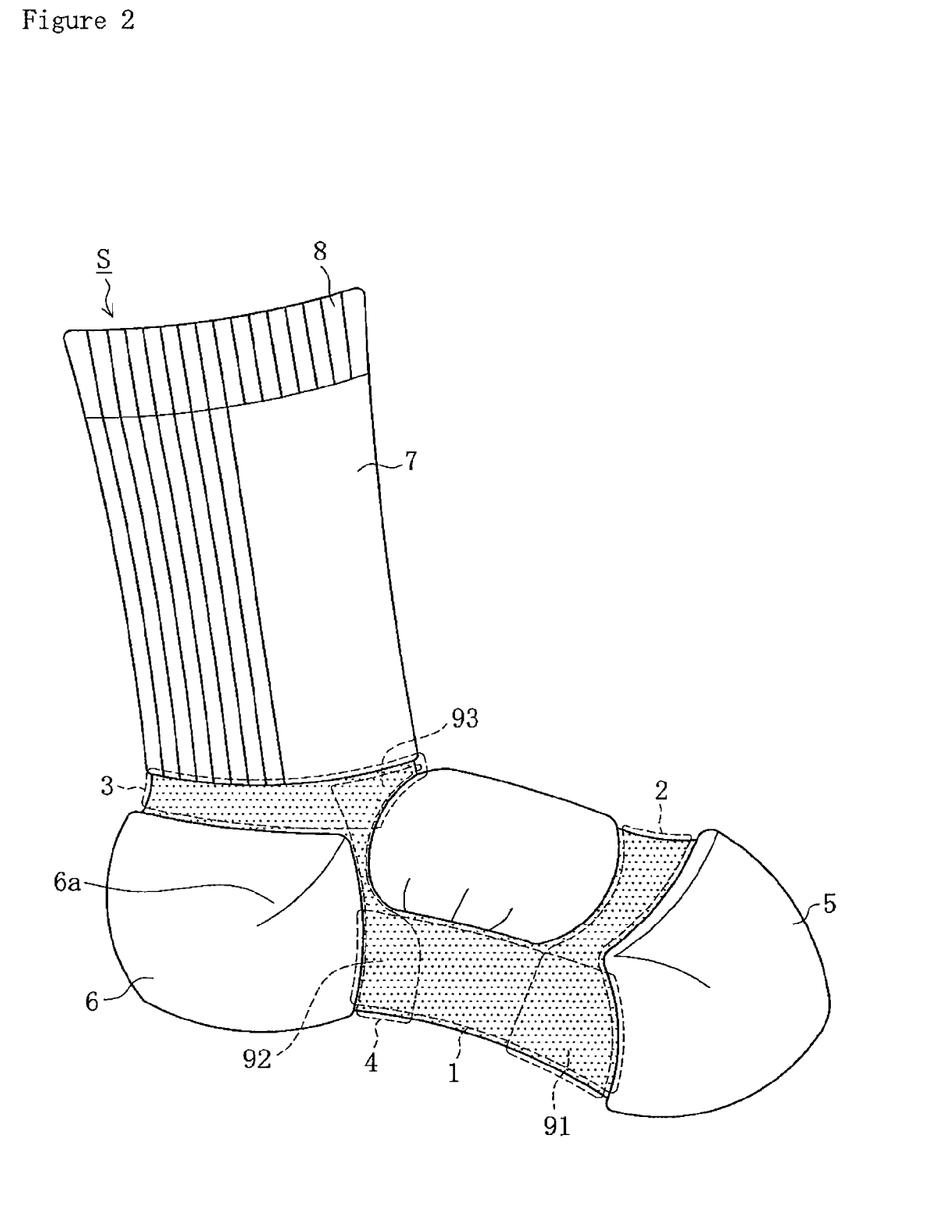
FIG. 2 is a lateral view of the same sock as seen from the side of the little toe.
Figure 3:
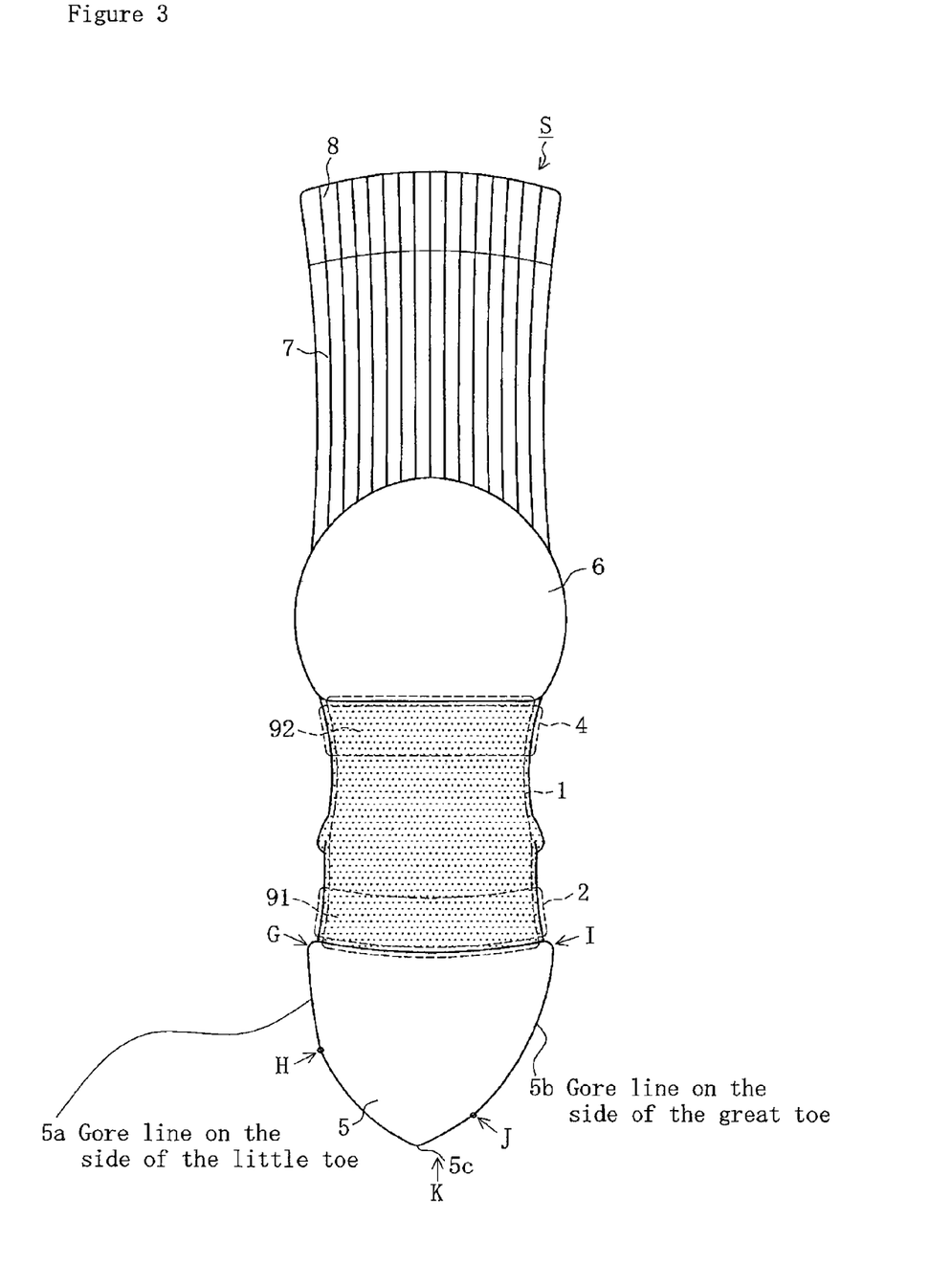
FIG. 3 is a view of the same sock as seen from the side of the sole portion.
Figure 4:
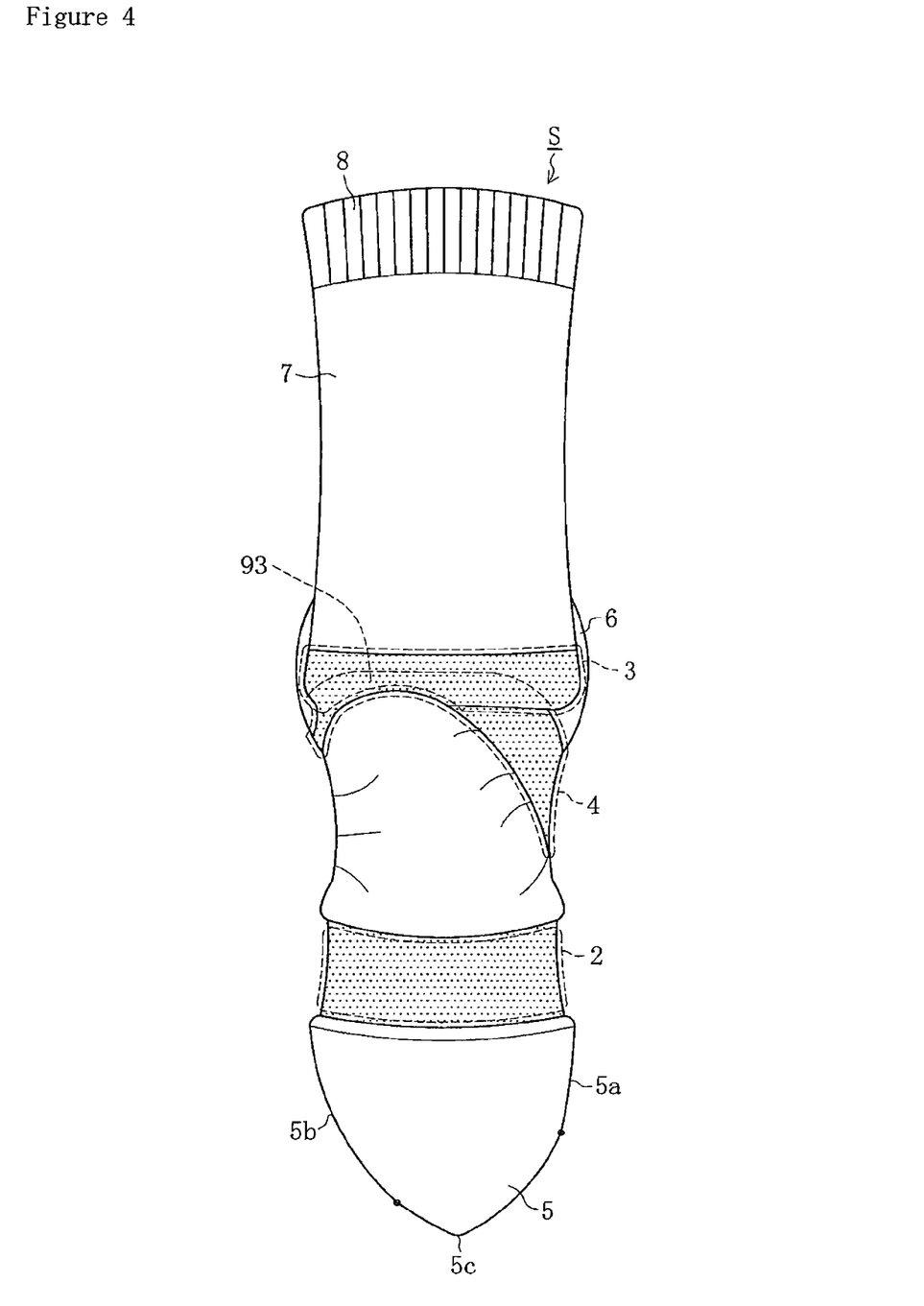
FIG. 4 is a view of the same sock as seen from the side of the instep portion.
Figure 5:
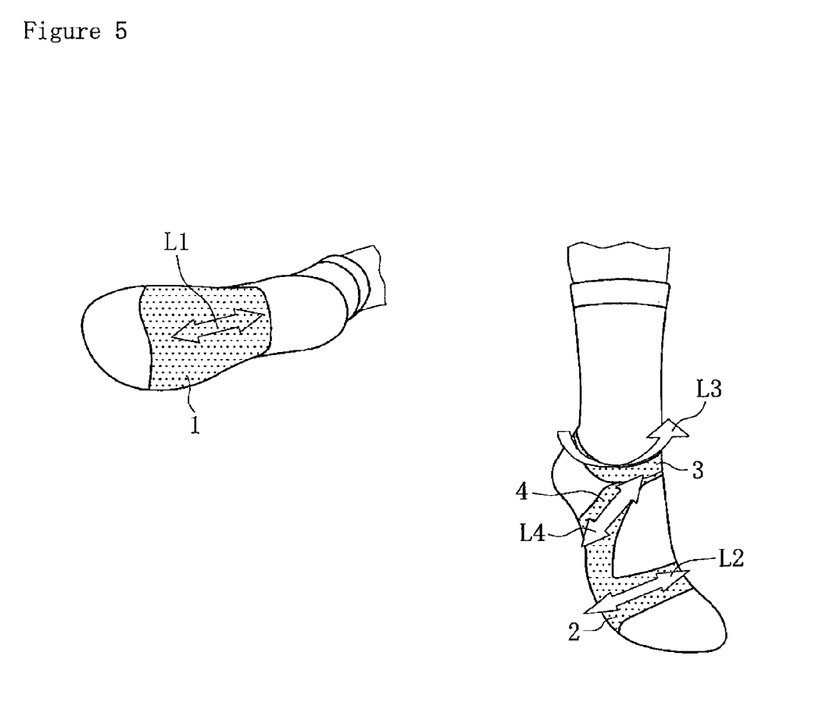
FIG. 5 is a drawing illustrating the direction of compression of the first through the fourth compression areas.

The sock of the present invention is described in further detail below based on the following example. FIG. 1 is a lateral view of a sock of an embodiment of the present invention for the right foot as seen from the side of the big toe. FIG. 2 is a lateral view of the same sock as seen from the side of the little toe. FIG. 3 is a view of the same sock as seen from the side of the sole portion. FIG. 4 is a view of the same sock as seen from the side of the instep portion. FIG. 5 is a drawing illustrating the direction of compression for the first through the fourth compression areas.

As shown in FIG. 1, a sock S of this example is provided with a first compression area 1 which raises the compressive force in a wale direction from a position A behind the toe area of a sole portion of the sock to a position C which includes the boundary between an arch portion B and a heel portion 6, a second compression area 2 provided on the periphery to raise the compressive force in a course direction at the position A behind the toe area, a third compression area 3 provided on the periphery to raise the compressive force in a course direction at an ankle portion D, and a fourth compression area 4 provided on the periphery to raise the compressive force in a course direction from the position C which includes the boundary between the arch portion B and the heel portion 6 to a position E at the base of the instep portion. In FIG. 1, Reference Numeral 5 is a toe portion, Reference Numeral 7 is a leg portion, and Reference Numeral 8 is an elastic welt, respectively.

Here, the "position behind the toe area" which is the starting position of the first compression area 1, refers to the position of a line connecting the ball of the big toe and the ball of the little toe at the base of the toes (indicated by A in FIG. 1).

The sock S of this example is provided with a second compression area 2 at the position of the anterior arch of the transverse plantar arch, and is also provided with a fourth compression area 4 at the position of the primary arch of the transverse plantar arch, thereby making it possible to obtain a compressive effect in the course direction at each respective position. As a result, a supporting effect can be achieved so that the shape of the transverse plantar arch does not change, and also, it is possible to achieve an effect of restoring the arch of the transverse plantar arch, which was lowered by vigorous or long-term activity.

In the sock S of this example, since the first compression area 1, securely positioned by the second compression area 2 and the fourth compression area 4, pushes up the longitudinal plantar arch from below, there is obtained the advantageous effect of protecting and restoring the shape of the longitudinal plantar arch.

In addition, an immobilizing action is produced at the position of the ankle portion by means of the third compression area 3 provided at the ankle portion, whereby the entire sock is restrained from slipping forward and backward, so that a stabilizing effect is obtained for the first through the fourth compression areas when the sock is worn. Furthermore, since a suitable compressive force is imparted to the ankle portion, support is given to the force produced when the foot hits the ground to generate thrust for walking, thereby making possible a pleasant walking motion.

In the sock S of this example, the first compression area 1 and the second compression area 2 are continuous in a region shown by Reference Numeral 91 at position A behind the toe area on the sole of the foot. Furthermore, the first compression area 1 and the fourth compression area 4 are continuous in a region shown by Reference Numeral 92 at a position C, which includes the boundary between the arch portion B and the heel portion 6. Moreover, the fourth compression area 4 and the third compression area 3 are continuous in a region down by Reference Numeral 93 from the position E of the base of the instep portion to the ankle portion D without separating, leaving a region 9 in the instep portion separating the second compression area 2 and the fourth compression area 4 as shown in FIGS. 1, 2 and 4. Accordingly, since the first compression area 1 through the fourth compression area 4 are made to be continuous, the various compression areas are mutually positioned to be able to reliably prevent slipping of the sock when the sock is worn.

The sock S of this example employs tuck knitting for a knit structure with increased expandability as a means for raising the compressive force of the first compression area through the fourth compression area, and employs "FTY" in the back yarns as a material with high expandability. In addition, the compressive force is increased by embedding rubber yarns. "FTY" is a fiber with nylon fibers or polyester fibers covering polyurethane fibers.

By using both a knit structure with high expandability and a material with high expandability, it becomes possible to achieve the sock of the present invention by a typical sock knitting process using a sock knitting machine, without separately employing a special process such as adhering or attaching an elastic member. Furthermore, even though the shape of the foot of the sock wearer varies from person to person, the response range broadens due to a synergetic effect of compressive force of the knit structure due to tuck knitting and the compressive force of the material due to the rubber yarns, thereby making it possible to impart sufficient compressive force to the various compression areas.

The rubber yarns used are elastic yarns having core yarns with a thickness of 400 D. In this case, it is suitable because the compressive force of the various compressive areas is maintained, even with repeated wearing, washing, and drying.

FIG. 2 is a lateral view of the sock S of this example as seen from the side of the little toe. In this example, the tensile force of the fabric of the first compression area 1 through the fourth compression area 4 is 5.0 N in the wale direction, and 7.0 N in the course direction. In this case, there is no impairment of the circulation of the foot, and sufficient compressive force is produced to protect and restore the shape of the longitudinal plantar arch and the transverse plantar arch of the bottom of the foot. It should be noted that in the various compression areas, the tensile force of the fabric may be identical in the wale direction and in the course direction, so the design of the sock does not become complex.

As shown in FIG. 1, the sock S of this example is provided with a gore line 6a which runs diagonally from a position at a starting point 6b in the vicinity of the anklebone to a position at the end 6c of the heel portion. In this example in particular, the heel portion 6 is constructed so as to cover the entire heel of the wearer of the sock, by having the starting point 6b of the gore line 6a approach the position E at the base of the instep portion, and making the gore line 6a deep. By so doing, the heel portion 6 completely encloses the entire heel, making it possible to obtain an effect such that slipping does not readily occur while the sock is worn.

In the sock S of this example, the inside surface of the toe portion 5 and the heel portion 6 are both knit with pile knitting, and the pile length of the heel portion 6 is made longer than the pile length of the toe portion 5. In this case, priority is given to the shock-absorbing capacity with a pile knit with longer piles for the heel portion 6, which receives the most impact when making contact with the ground during walking, and also, the use of pile knitting with piles of short length in the toe portion 5 upon which is exerted a force when the foot hits the ground to generate thrust for walking ensures that this force will be exerted, thereby making it possible to soften the impact on the toe portion 6 when this force is exerted.

FIG. 3 is a view of the sock S of this example as seen from the side of the sole portion. FIG. 4 is a view of the same sock as seen from the side of the instep portion. 5a is a gore line on the side of the big toe, and it has a length extending from the starting point G to the end H. 5b is a gore line on the side of the little toe, and it has a length extending from the starting point I to the end J.

As shown in FIG. 3, the sock S of this example is constructed so that in the toe portion 5, the gore line 5b on the little toe side is longer than the gore line 5a on the big toe side, and the front end 5c of the toe portion 5 is caused to shift to the big toe side from the position K of the tip of the third toe, and the end H of the gore line 5a on the big toe side is positioned on the inside of the big toe.

When constructed in this manner, the shape of the toe portion 5 of the sock is able to approximate the oblique foot shape which is prevalent among the Japanese people, and eliminates the tugging felt on the inside of the big toe when wearing the sock, thereby increasing the comfort.

In the sock S of this example, parts other than the first compression area 1 through the fourth compression area 4, such as the toe portion 5, the heel portion 6, a leg portion 7, and an elastic welt 8, are knit using yarns of cotton 32/3 three folded yarn of "Brantash" (Registered Trade Name, Toray Industries, Inc.) with excellent water absorption and quick-drying properties. This sock is therefore suitable for walking and jogging.

FIG. 5 is a diagram illustrating the directions in which the various compressive forces work. L1 shows compression in the wale direction of the first compression area 1 provided to the sole portion. L2 shows compression in the course direction of the second compression area 2 provided at the position of the anterior arch of the transverse plantar arch. L3 shows compression in the course direction of the third compression area 3 provided around the ankle portion. L4 shows compression in the course direction of the fourth compression area 4 provided at the position of the primary arch of the transverse plantar arch.

The following is an explanation of the methods and results of tests performed to verify the advantageous effects of the sock of the present invention. Verification tests were performed for three items: (A) Test to measure changes in arch circumference; (B) Test to evaluate inflammation of the sole; and (C) Fabric tensile test.

(A) Test to Measure changes in Arch Circumference

Figure 7:
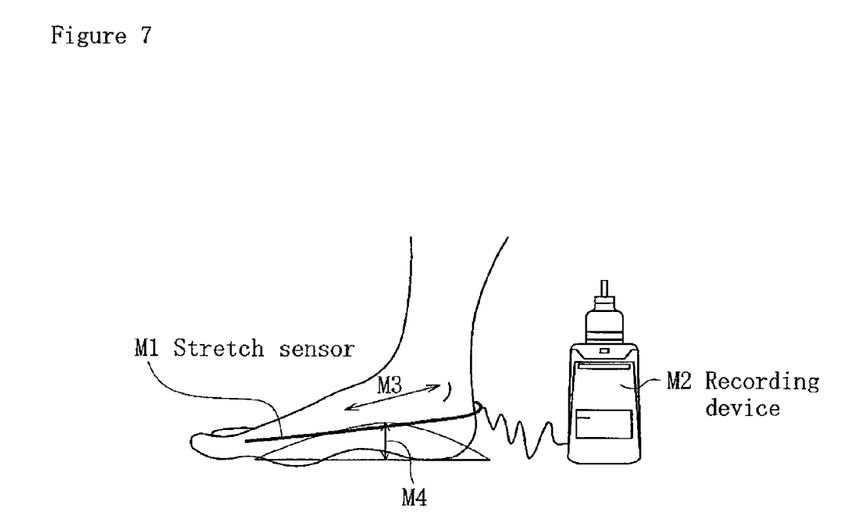
FIG. 7 is a schematic diagram illustrating the configuration of a stretch sensor and a recording device used in tests measuring changes in arch circumference.

As shown in FIG. 7, a stretch sensor M1 and a recording device M2 are used to determine to what extent the sock S of this example exhibits the advantageous effect of maintaining the shape of the arch of the bottom of the foot formed from the longitudinal plantar arch and the transverse plantar arch, by measuring changes in the arch circumference during walking. Measurement of the arch circumference is based on the area of the first metatarsal head to the edge of the calcaneus to the fifth metatarsal head (the length in the direction of arrow M3 in FIG. 7). Changes in the arch circumference signify changes in the skeletal structure of the foot. Specifically, if the arch circumference increases, the arch height (the length in the direction of arrow M4 in FIG. 7) decreases. If the arch circumference decreases, the arch height (the length in the direction of arrow M4 in FIG. 7) increases.

1) Test Method

Measurements of arch circumference during walking were made on 5 healthy adult subjects. The stretch sensor M1 was placed from a point at the first metatarsal head of the right foot, across a point on the edge of the calcaneus to a point at the fifth metatarsal head, applying a light tension. The end of the sensor was affixed with surgical tape. The subjects walked freely in a straight line for 1 minute, and the measurement data were recorded with the recording device M2.

In this test, a respiration pick-up (AP-C022, Futami ME Kogyo Co.), a sensor which measures respiration, was used as the stretch sensor M1 for measuring changes in the arch circumference. Within the stretch sensor M1 is a conductive substance, and the resistance changes as the sensor changes shape. Changes in potential can be measured as changes in voltage, according to changes in resistance. Since the sensor itself is short, garment elastic is attached to both ends of the sensor.

2) Test Results

Figure 8:
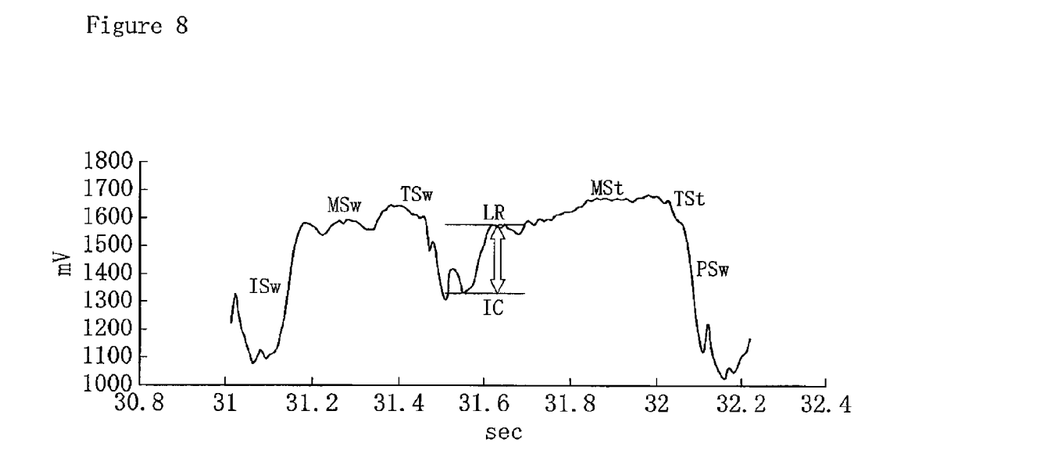
FIG. 8 is a graph showing changes in arch circumference on the bottom of a foot due to walking (output from a stretch sensor) in a time series, illustrating that the amount of change from when the heel touches the ground (IC) to the peak when the bottom of the foot touches the ground (LR) is in terms of amount of change in arch circumference when the subjects are standing.

TABLE 1 shows measurement results for arch circumference for 5 healthy adult males, with bare feet, and wearing the sock S of this example. It should be noted that, as shown in FIG. 8, the amount of change from when the heel touches the ground (IC) to the peak when the bottom of the foot touches the ground (LR) is computed as the amount of change in arch circumference when the subjects are standing.

TABLE 1

|  | Change in Arch Circumference While Standing |
|---|---|
| With bare feet | Average 2.9 ± 0.8 mm |
| Wearing sock of this example | Average 1.9 ± 0.6 mm |

As shown above, while the change in arch circumference with bare feet averaged 2.9±0.8 mm, the change in the arch circumference averaged 1.9±0.6 mm when the sock S of this example was worn. Accordingly, the sock of the present invention was found to have an arch-maintaining effect in comparison to when the feet are bare, since the results show that changes in the arch circumference are restrained.

(B) Test to Evaluate Inflammation of the Sole

The occurrence of inflammation was evaluated by measuring the soles of the feet by thermography after long-term walking, in order to determine to what extent the sock S of this example had the effect of reducing the load on the bottom of the human foot. When inflammation occurs on the bottom of the foot, blood collects, and the temperature rises.

1) Test Method

Inflammation of the bottom of the foot after walking was evaluated in 10 healthy adult subjects. Subjects walked freely outdoors for 3 hours, wearing the sock S of this example and an ordinary plain knitted sock, one on the left foot and one on the right foot. After walking, the feet were immersed for 10 seconds in cold water at 10° C., and after wiping thoroughly, the bottoms of the feet were observed with thermography. Thermography was performed with an NEC Sanei Co. Thermotracer TH5102. Results were determined by comparing the temperature of the right foot and the left foot.

2) Test Results

The results of evaluation of inflammation of the bottoms of the feet of the 10 healthy adult subjects showed a clear difference between the right and left feet of 6 of the 10 subjects, and inflammation was suppressed on the bottoms of the feet of subjects wearing the sock S of this example. The results for the remaining 4 subjects could not be clearly determined, but it cannot be said that there was no effect. These results confirm that although there are individual differences, the sock of the present invention reduced the load on the bottoms of the feet.

(C) Fabric Tensile Test

The following test was performed to determine the compressive force of the various compression areas of the sock S of this example.

1) Test Method

The fabric was cut into 2.×7 cm test pieces, and using a tensile tester (AUTOGRAPH AGS-H, Shimazu), the stress was measured when the elongation was 60%. After stretching and recovery were repeated twice, the measured values from the second time were used. The test was performed three times, an average value was obtained, and this value was used for the evaluation. The tensile speed was 300 mm/min. The testing environment was 20° C. and 65% RH.

2) Test Results

While determining the tensile force of fabric using the above test method, an analysis was made of the relationship (lower limit value) between the range within which favorable results are obtained with test (A) for measuring changes in the arch circumference and the tensile force of the fabric. If the tensile force is too great, the compression is too great and the sock is uncomfortable to wear, and since there is a risk that circulation will worsen, the opinion of the monitors was sought, and an analysis was made of the suitable range for tensile force (the upper limit). As a result, a tensile force in the longitudinal direction (wale direction) of 3.5-6.0 N, and a tensile force in the transverse direction (course direction) of 5.0-9.0 N were determined to be most desirable.

As described above, the sock of the present invention is provided with a second compression area at the position of the anterior arch of the transverse planar arch, and a fourth compression area is provided at the primary arch of the transverse plantar arch, so a compressive effect is obtained in the course direction at the respective positions, thereby producing the advantageous effects of protecting and restoring the shape of the transverse plantar arch. Furthermore, since the first compression area, which is securely positioned by the second compression area and the fourth compression area, pushes up the longitudinal plantar arch from below, there is obtained the advantageous effect of protecting and restoring the shape of the longitudinal plantar arch, so that the entire sock is restrained from slipping forward and backward by the third compression area provided at the ankle portion, thereby stabilizing the various compression areas while the sock is worn.

Therefore, according to the present invention, it is possible to solve the problems of conventional socks: (1) The problem that no consideration was given to protecting and restoring either the longitudinal plantar arch or the transverse plantar arch, and (2) The problem that it was impossible to continuously apply a compressive force at the desired positions, since the positions of the compressive areas slipped while the sock was being worn.

Furthermore, due to the fact that a construction such as that described above is used, the sock of the present invention protects a group of plantar muscles which is soft tissue of the sole of the foot, and also protects the plantar fascia (plantar aponeurosis), and has the effect of supporting the shape of the arch. Moreover, it distributes the load during expansion and contraction of the soft tissue of the sole of the foot, and by handling the load in this manner, it reduces the load on the soft tissue of the sole of the foot. In addition, it prevents inflammation by reducing the load on the plantar aponeurosis, supports the force produced when the foot hits the ground to generate thrust for walking by increasing the shock-absorbing capacity, and has the effect of creating a smooth walking or running motion.

The present invention is not limited to the above examples, and the embodiments can be suitably modified, as long as they are within the scope of the technical ideas recited in the claims.

The sock of the present invention is not limited to general use, but it can also be used in socks for golf, tennis, jogging, walking, and other sports.

We claim:

1. A sock comprising high compressive force areas knit with a material having high expandability and a relatively lower compressive force areas knit without the material having high expandability, the high compressive force areas comprising:
   a first compression area being extensive over a sole portion of a sock in a wale direction and having a front end positioned at a front end of an arch portion of the sock located behind a toe area of the sock and a rear end positioned at a rear end of the arch portion which includes a boundary between the arch portion and a heel portion of the sock, the first compression area being adapted to exert longitudinal compressive force in the wale direction over the sole portion between the front and rear ends of the arch portion;
   a second compression area provided in a course direction circumferentially through the front end of the first compression area and a front end of an instep portion of the sock and adapted to exert transverse compressive force in the course direction over the sole portion at the front end of the arch portion;
   a third compression area provided in a course direction circumferentially through a base of an instep portion and an ankle portion of the sock; and
   a fourth compression area provided in a course direction circumferentially through the rear end of the first compression area and a rear end of the instep portion and adapted to exert transverse compressive force in the course direction over the sole portion at the rear end of the arch portion, wherein when the sock is worn, the second and fourth compression areas cooperate to position the first compression area relative to a foot in the sock, and
   the relatively lower compressive areas comprising a specific lower compressive region extensive in the instep portion of the sock between the second and fourth compression areas, the lower compressive region being designed to exert a longitudinal compressive force smaller than the longitudinal compressive force exerted by the first compression area to thereby cooperate with the first compression area and provide a difference in compressive force between the lower compressive region and the first compression area, when the sock is worn, to push up and support a longitudinal plantar arch of the foot.

2. A sock according to claim 1, wherein the fourth compression area and the third compression area are made continuous from the position of the base of the instep portion to the ankle portion.

3. A sock according to claim 1, wherein the first through the fourth compression areas have the compressive force increased in a desired direction by using a knitted structure with increased expandability.

4. A sock according to claim 3, wherein the first through the fourth compression areas are knit using tuck knitting for a knit structure with increased expandability, and the material with high expandability comprises at least one of rubber yarns and FTY.

5. A sock according to claim 4, wherein the rubber yarns are elastic yarns having core yarns with a thickness of 120 D-680 D.

6. A sock according to claim 1, wherein the first through the fourth compression areas, have a tensile force in the wale direction of the fabric within a range of about 3.5 to about 6.0 N, and a tensile force in the course direction of the fabric within a range of about 5.0 to about 9.0 N.

7. A sock according to claim 6, wherein the tensile force of the fabric of the first through the fourth compression areas is the same tensile force.

8. A sock according to claim 1, wherein a gore line on a little toe side is made longer than on a big toe side, and a front end of the toe portion is shifted from a position of a tip of a third toe to a side of the big toe, and an end of the gore line on the big toe side is positioned on an inner side of the big toe.

9. A sock according to claim 8, wherein a shape of the toe portion, when viewed from a planar perspective, is formed in an oblique shape.

10. A sock according to claim 1, further comprising a gore line which runs diagonally from a starting point in a vicinity of an anklebone to an end of a heel portion, wherein the heel portion is made to cover the entire heel, by having a starting point of the gore line approach the position of the base of the instep portion.

11. A sock according to claim 1, wherein an inside surface of the toe portion and the heel portion are both knit with pile knitting, and a pile length of the heel portion is made longer than a pile length of the toe portion.

12. A sock according to claim 1, wherein components other than the first through the fourth compression areas are knit with two or more highly water-absorbent and quick-drying materials including polyester, acrylic, wool, rayon, or cotton.

* * * * *